United States Patent [19]
Heilmann et al.

[11] Patent Number: 5,268,144
[45] Date of Patent: Dec. 7, 1993

[54] METHOD FOR STERILIZING A MEDICAL UNIT

[75] Inventors: Klaus Heilmann, St. Wendel; Bernd Mathieu, Spiesen-Elversberg; Michael Rink, St. Ingbert-Hassel; Wolfram Weber, Spiesen-Elversberg, all of Fed. Rep. of Germany

[73] Assignee: Fresenius AG, Fed. Rep. of Germany

[21] Appl. No.: 921,907

[22] Filed: Jul. 29, 1992

Related U.S. Application Data

[62] Division of Ser. No. 608,560, Nov. 2, 1990, Pat. No. 5,147,613.

[30] Foreign Application Priority Data

Nov. 4, 1989 [DE] Fed. Rep. of Germany ....... 3936785

[51] Int. Cl.$^5$ .......................... A61L 2/06; A61L 2/16
[52] U.S. Cl. ....................................... 422/26; 422/27; 422/28; 422/31; 210/636
[58] Field of Search ................... 422/1, 25, 26, 27, 28, 422/31; 134/3, 30, 31, 37; 210/140, 321.69, 636

[56] References Cited

U.S. PATENT DOCUMENTS

| | | | |
|---|---|---|---|
| 3,753,493 | 8/1973 | Mellor | 210/140 |
| 3,871,913 | 3/1975 | Shaldon | 210/321.69 |
| 4,018,684 | 4/1977 | Uffer | 210/140 |
| 4,158,034 | 6/1979 | Riede et al. | 422/36 |
| 4,166,031 | 8/1979 | Hardy | 210/22 A |
| 4,176,156 | 11/1979 | Asanuma et al. | 422/25 |
| 4,209,402 | 6/1980 | Gentles | 210/137 |
| 4,332,264 | 6/1982 | Gortz et al. | 134/57 R |
| 4,366,051 | 12/1982 | Fischel | 210/96.2 |
| 4,399,030 | 8/1983 | Hlavinka et al. | 210/91 |
| 4,411,866 | 10/1983 | Kanno | 422/25 |
| 4,517,081 | 5/1985 | Amiot et al. | 210/140 |
| 4,673,506 | 6/1987 | Henne et al. | 210/636 |
| 4,695,385 | 9/1987 | Boag | 210/636 |
| 4,728,496 | 3/1988 | Petersen et al. | 422/1 |
| 4,767,538 | 8/1988 | Jakubowski et al. | 210/636 |
| 4,810,469 | 3/1989 | Masuhara | 422/26 |
| 4,840,769 | 6/1989 | Nejigaki et al. | 210/636 |
| 4,857,181 | 8/1989 | Shouldice et al. | 210/87 |
| 5,015,374 | 5/1991 | Mathieu et al. | 210/232 |

FOREIGN PATENT DOCUMENTS

| | | |
|---|---|---|
| 370850 | 5/1990 | European Pat. Off. . |
| 3324414 | 1/1985 | Fed. Rep. of Germany . |
| 3425412 | 1/1986 | Fed. Rep. of Germany . |
| 3708733 | 10/1987 | Fed. Rep. of Germany . |
| 3708734 | 10/1987 | Fed. Rep. of Germany . |

Primary Examiner—Robert J. Warden
Assistant Examiner—T. A. Trembley
Attorney, Agent, or Firm—Marshall, O'Toole, Gerstein, Murray & Borun

[57] ABSTRACT

This invention relates to a method for sterilizing a medical unit having at least two connections for a fluid flow pathway where a sterilizing medium flows through the medical unit.

Medical units of this type are e.g. medical filters, in particular dialyzers. A high degree of sterility is here required. This is accomplished through the steps of:

(a) inserting the medical unit into a system under pressure-tight coupling of the at least two connections to a feed conduit and discharge conduit of the system under atmospheric conditions;

(b) passing the sterilizing medium from the system through the medical unit for a given period of time;

(c) closing the at least two connections in the coupled state and in a germproof manner, without the same being opened, on completion of the sterilization operation; and (d) removing said medical unit from said system as a sterile medical unit with closed connections.

All steps, including the removal of the medical unit, are therefore carried out in a system where the sterility obtained is constantly maintained. This "inline sterilization" guarantees a high degree of sterility of the medical units treated.

23 Claims, 4 Drawing Sheets

TO INSTALLATION (PLANT, EQUIPMENT)

METHOD FOR STERILIZING A MEDICAL UNIT

CROSS-REFERENCE TO RELATED APPLICATION

This is a division of copending, commonly assigned application Ser. No. 07/608,560 filed Nov. 2, 1990, now U.S. Pat. No. 5,147,613, issued Sep. 15, 1992, the entire disclosure of which is incorporated herein by reference.

BACKGROUND OF THE INVENTION

This invention relates to a method for sterilizing a medical unit comprising at least two connections for a fluid flow pathway where a sterilizing medium flows through the assembly.

The present invention also relates to an apparatus for carrying out this method with a means used for producing and/or providing the sterilizing medium in the system.

Medical units of this type, such as medical filters, in particular blood treating filters which are inserted into the extracorporeal circuit (e.g. dialyzers) must always be as sterile as possible. The same applies to units which are used for applying sterile medicaments.

It is known in practice that medical units of this type are sterilized in sequential steps to make them ready for delivery. The individual steps are carried out separately in different rooms or systems, so that there are unsterile intermediate steps between the individual steps, resulting in a possible loss of sterility.

In the method known from U.S. Pat. No. 4,411,866 (corresponding to German DE 30 12 110 A1), the disclosure of which is hereby incorporated by reference, an artificial kidney is first filled up with a fluid which is not harmful to the human body. The connections of the kidney are then closed. The artificial kidney which is already accommodated in a packing container is subsequently introduced into an autoclave and sterilized in steam at an elevated temperature and under high pressure.

Considerable typical disadvantages of the known kind of method are:
Expensive, expandable special closures or expansion chambers are necessary for compensating for the increase in volume during sterilization in the autoclave;
the closures may nevertheless tear;
not every type of artificial kidney can be sterilized in accordance with the known method;
since the sterilizing operation is carried out with a "quasi-stagnant liquid" in the artificial kidney, non-sterile pockets may be formed with heat bridges in dead corners.

The method which has become known from U.S. Pat. No. 4,810,469 (European Patent Application EP 0 198 100 A1), herein incorporated by reference, goes one step further. In this method an artificial human organ, such as an artificial kidney, is continuously sterilized in an autoclave, namely from the inside with water heated to a sterile temperature and from the outside with superheated steam. The organ is subsequently cooled by a correspondingly cool sterile water, which inwardly flows through the organ, whereby the sterile condition is maintained.

The present invention starts from this known method in which the sterilization operation is carried out continuously.

A considerable disadvantage of the known method and the associated apparatus is that the sterile state might be abandoned when the artificial organ is removed from the autoclave for closing and packaging the same.

OBJECT UNDERLYING THE INVENTION

It is the object of this invention to develop the above-mentioned method and apparatus such that unsterile intermediate steps are avoided.

SUMMARY OF THE INVENTION

This object is attained with the method of the invention by the following steps:
(a) Inserting the unit into a system under pressure-tight coupling of the two connections to a feed conduit and discharge conduit of the system under atmospheric conditions;
(b) passing the sterilizing medium from the system through the unit for a given period;
(c) germproof closing of the two connections in the coupled state, without the same being opened, after completion of the sterilization operation; and
(d) removing the unit from the system as a sterile unit with closed connections.

This object of the invention is attained with the apparatus by:
at least one fastening means which is subjected to atmospheric pressure and used for the temporary pressure-tight coupling of the unit connections and comprises an inlet and an outlet;
at least one conduit from the sterilizing medium means to the inlet of the fastening means;
at least one conduit which is connected to the outlet of the fastening means;
closing members, in particular shut-off valves, in the conduits;
closing of the connections of the unit in the coupled state.

Hence, in the method and apparatus of the invention sterilization is performed "inline", i.e. all treatment steps are carried out in the same system in which the treating means also flow through. This avoids any unsterile intermediate steps and ensures that patients obtain medical units which are aseptically closed with the highest possible degree of safety.

Suitable sterilizing media are conventional media, such as pressurized water or water vapor of at least 105° C., depending on the compatibility with the respective medical unit. A peracetic acid solution may advantageously be used as a sterilizing medium for hydrophobic units.

A flushing step prior to and/or after the sterilizing step is necessary with specific medical units in conjunction with the sterilizing medium to be used. Water which must be sterile itself in a flushing step after sterilization is preferably used as the flushing fluid.

In a closed system with pressurized water or superheated steam as the sterilizing medium, the flushing water may be derived from the sterilizing medium. For instance, the water which is not yet heated to high temperatures serves as the flushing fluid prior to the sterilization step, and cooled pressurized water or condensed water vapor is used as the flushing fluid after sterilization.

Depending on the medical unit used, it may be expedient to leave the unit filled with sterile fluid when it is closed, or to interpose a drying step with sterile gas, such as air, which is heated to at least 100° C. if necessary.

Hence, there are various possibilities of combination which depend on the respective medical unit.

With hydrophilic units, such as cuprophane dialyzers, the method is performed in the following way: The flushing operation is carried out with hot water. The hot water is subsequently heated to a sterile temperature under pressure and the sterilization step is then carried out as a heat sterilization with this pressurized, circulating water. The circulating pressurized water is subsequently cooled to room temperature and the medical unit is then closed under sterile conditions.

With a hydrophobic unit, such as a polysulphone membrane filter, the method is advantageously performed such that the flushing operation is carried out with hot water, the sterilization step is then carried out with water vapor as the heat sterilization medium and the medical unit is subsequently closed under sterile conditions After heat sterilization the unit is expediently postflushed with sterile water and subsequently dried.

As an alternative to this method using pressurized water, the flushing operation is performed with hot water, the sterilization step is then carried out with circulating peracetic acid at room temperature, the medical unit is then flushed with sterile water and subsequently closed under sterile conditions.

The apparatus offers corresponding possibilities of combination.

The present invention shall now be explained in greater detail with reference to the embodiments which are shown in the drawings and relate to the dialyzers as medical units Variations and modifications of the invention will also become apparent therefrom.

Figure 1:
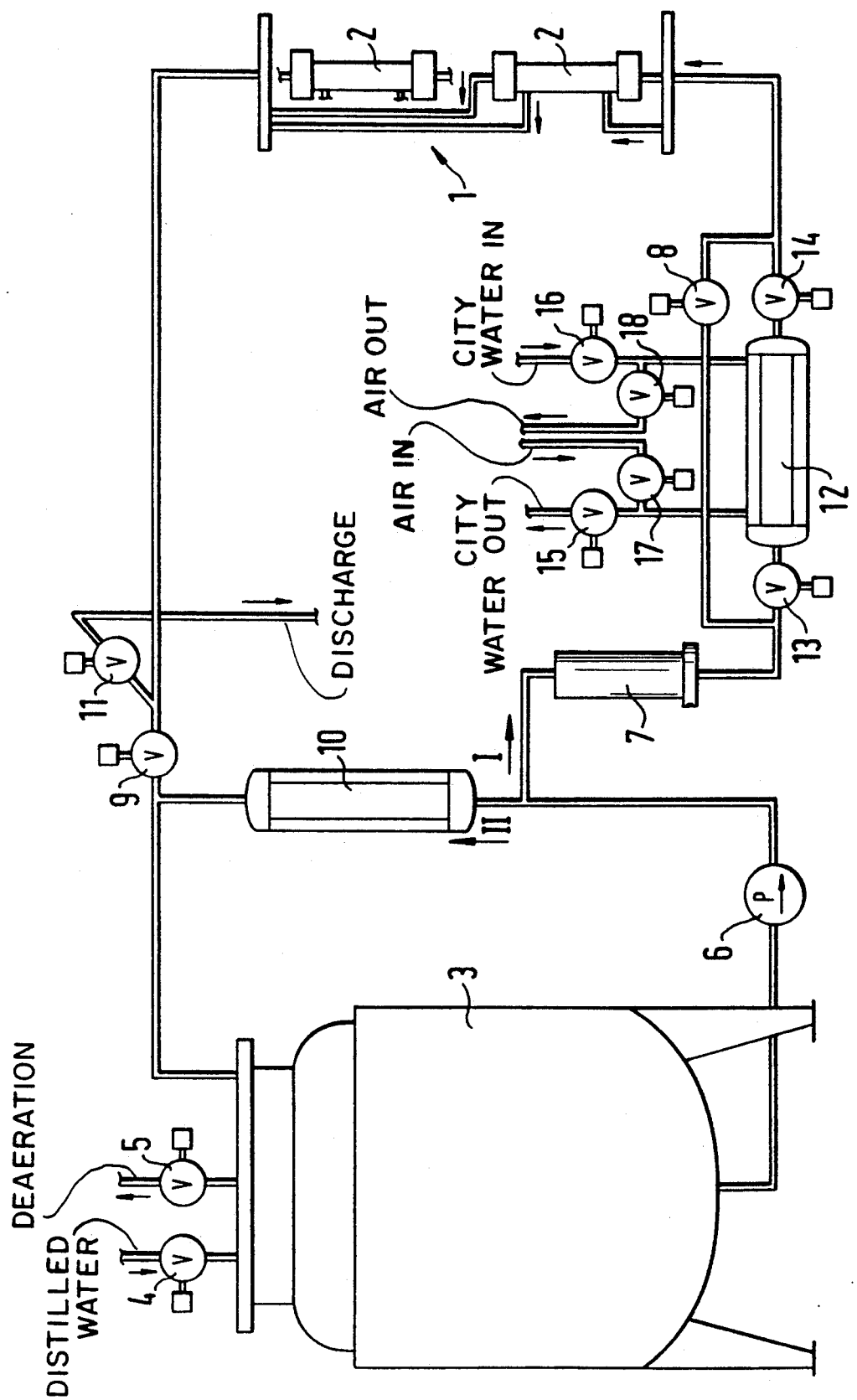
FIG. 1 depicts a sterilization system for dialyzers with pressurized water as the sterilizing medium.

The sterilization system shown in FIG. 1 serves to sterilize regenerated cuprophane dialyzers by means of pressurized water at a temperature of preferably 121° C.

Dialyzers 2 (preferably 10 pieces) which are to be sterilized and respectively positioned on a special steel sheet, which has been subjected to grinding, are each inserted into a respective fastening means, which holds the dialyzer in place, and firmly connected to the flushing connections of the fastening means with their open closure ends at the blood and dialysate sides. A connection technique as set forth in U.S. Pat. No. 5,015,374 issued May 14, 1991 (corresponding to German patent application P 38 25 573), the disclosure of which is hereby incorporated by reference, is preferably employed.

Distilled water having a temperature of 123° C. is held ready in a container 3. Container 3 comprises a valve 4 for feeding distilled water and a valve 5 for venting the container. The container is under increased pressure, so that the water cannot boil at the predetermined temperature.

The hot pressurized water is withdrawn from the container by means of a circulating pump 6. A partial flow I passes through a filter element 7 having a filter pore size 10 $\mu$m and a first circuit valve 8 through dialyzers 2 to be sterilized and another circuit valve 9 back into container 3. Another partial flow II is constantly passed through a heat exchanger 10 back into the container and serves to keep the container temperature constant.

Another valve 11 which is connected to an outlet is provided downstream of the dialyzer fastening means.

Filter element 7 and fastening means 1 for the dialyzers have arranged therebetween a cooler 12 with upstream and downstream valves 13, 14, in the bypass to the circuit. At the cooling side, cooler 12 is provided with valves 15, 16 for the inlet and outlet of cooling water (town or tap water) and with valves 17, 18 used for aerating and venting.

The sterilization process is carried out in a plurality of steps.

1. Insertion of the Dialyzers

All closing caps of dialyzers 2 are so turned that entire locking and sealing are ensured The closing caps - two caps for the blood side and two caps for the dialysate side for each dialyzer - include an O ring and an inserted plug (according to U.S. Pat. No. 5,015,374 issued May 14, 1991, incorporated by reference German DE 38 25 573 A1.

The dialyzers are then inserted into the receiving device of fastening means 1 comprising sealing cylinders for the dialyzer caps.

2. Flushing

After dialyzers 2 have been inserted into the fastening means, valves 5, 11, 13, 14 are opened. The other valves are closed. Dialyzers 2 and cooler 12 are flushed with hot pressurized water of about 98° C. for a specific time interval (about 4 minutes), with the flushing water being directly passed into the outlet and thus removed from the entire circuit. In the flushing phase the temperature continually increases due to heating by means of heat exchanger 10 in tank bypass II.

3. Sterilization

On completion of the flushing operation, after which valves 13 and 14 remain open while valves 8 and 9 are additionally opened, the pressurized water is heated to a sterilization temperature of about 123° C. The heating phase is designed such that after its end (i.e. approximately 10 minutes) at least a temperature of 121° C. is indicated at all measuring points. The hot pressurized water is continuously circulated by means of circulating pump 6 via filter element 7 and dialyzers 2 back into container 3. The sterilization operation, including the heating step, lasts 30 minutes. It must be ensured that at least a temperature of 121° C. prevails at all measuring points during the entire duration of the sterilization phase.

4. Cooling

After sterilization the pressurized water is cooled to room temperature by switching on the previously sterilized cooler 12 via valves 15 and 16. Circuit valve 8 is closed at the same time. The pressurized water is here conveyed in cooled form through the dialyzers which are thereby also cooled to room temperature. The post-cooling temperature in the blood port of the dialyzer is somewhat lower than that in the dialysate part (25° compared with 20°).

5. Closing and Removal

After cooling, the dialyzer is automatically closed by pneumatically driving the plug into the closing caps and is removed from fastening means 1 by releasing and retracting the holding cylinders. The cooled sterile water remains in the sterile dialyzer.

Figure 2:
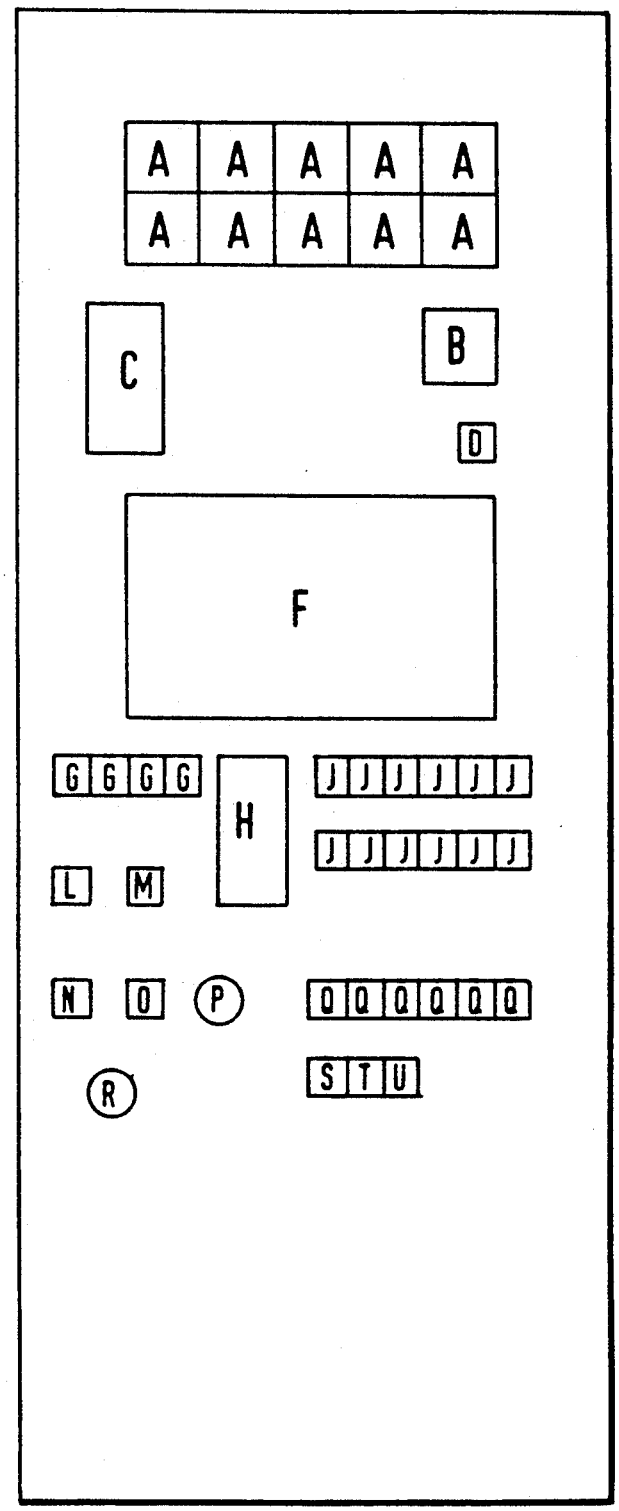
FIG. 2 shows the control panel of a program control for controlling the system of FIG. 1.

The sterilizing system can be controlled manually or automatically by alternatively switching on a mode switch. During manual operation the valves are individually controllable. During automatic operation, the valves are time- and temperature-controlled by a program control. Such program controls which successively control individual process steps in time- and sensor-controlled fashion are known to those skilled in the art. The associated control panel is expediently designed in accordance with FIG. 2 and contains the following display and control elements which are respectively marked with a letter in FIG. 2 and connected to the associated sensors or control parts.

- A digital displays for temperature
- B digital display for container temperature
- C level display
- D change-over switch, temperature display for blood and dialysate
- F recorder for pressure and temperature
- G control lamps for pumps
- H controller for heating temperature
- I change-over switch, manual-zero automatic for pneumatic valves
- L switch for backing pump
- M switch for pump
- N key "start"
- O key "stop"
- P "emergency switch"
- Q program indicator lamps
- R main switch
- S key "fastening"
- T key "closing"
- U key "removal"

During automatic operation the sterilization system is therefore operated and adjusted as follows:

The dialysis filters, e.q. 10 pieces, are inserted into ten fastening means and connected to the system by pressing key S marked "fastening". The automatic sequence is started by pressing key N "start". The individual program steps—flushing, sterilizing, cooling, closing and removal—are successively and automatically carried out in program-controlled fashion according to the set time.

The individual program steps are indicated by indicator lamps Q during the running of the program. The temperatures of all dialyzers are indicated by digital displays A—by means of change-over switch D alternatively at the blood and dialysate sides—and recorder on recorded F for documentation purposes. The program is terminated when the lamp "end" lights up. After keys T "closing" and U "removal" from the fastening means.

After new dialyzers have been inserted into the fastening means, the process can be started again.

In the embodiment of FIG. 1 depicting cuprophane dialyzers, hot and distilled pressurized water of at least 121° C. is used as the sterilizing medium. Instead of pressurized water, a 3% peracetic acid may also be used at room temperature as the sterilizing medium. In this case the dialyzers must be flushed with sterile water after the sterilization operation to free them from the sterilizing medium.

Figure 3:
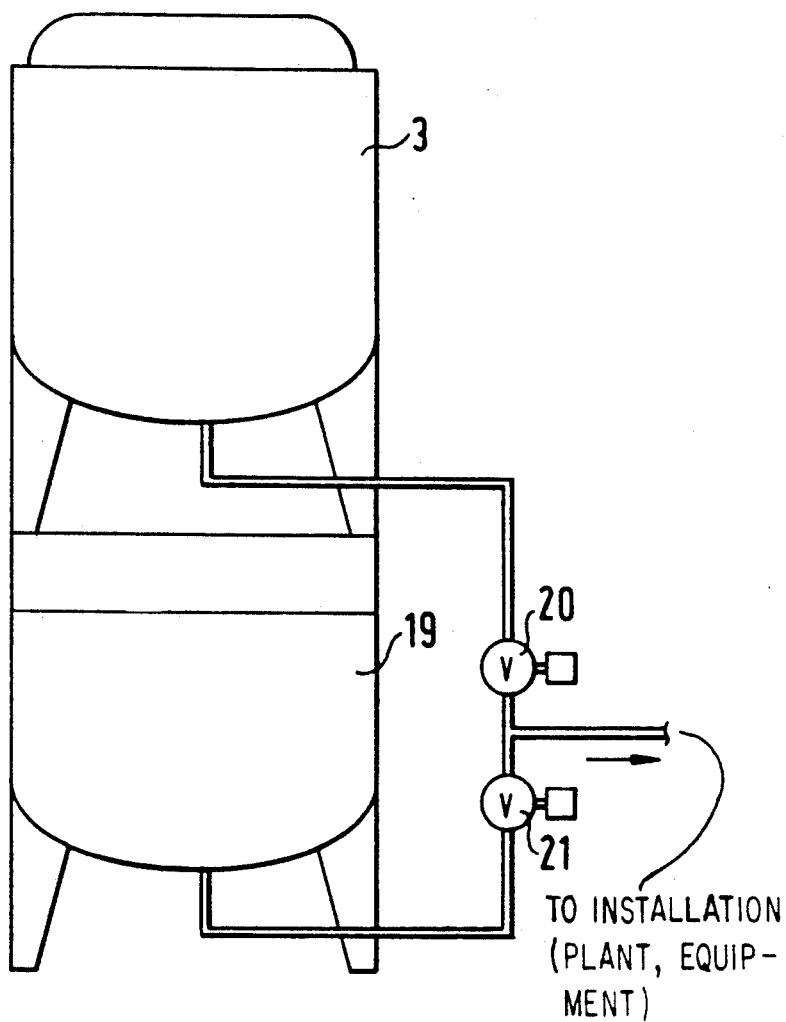
FIG. 3 is a sectional view of the system shown in FIG. 1, with alternatively adjustable tanks for different sterilizing media.
Figure 3A:
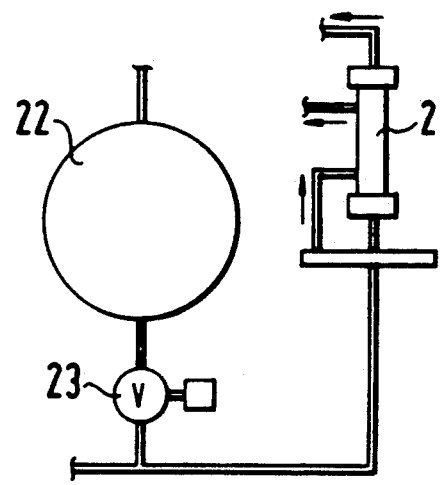
FIG. 3a shows a section of the system in FIG. 1 with a container for sterile air for drying the dialyzers.

From the technical point of view it may be expedient—as shown in the sectional view of FIG. 3—to provide containers 3, 19 for two sterilizing media which can be supplied alternatively via associated valves 20, 21. Tank 3 containing hot water may here serve as a source of sterile water for flushing the dialyzer after its sterilization so as to free it from peracetic acid supplied from container 19. After flushing with sterile water, dialyzers 2 may be dried by feeding sterile air from a container 22. The air can be supplied into the system via valve 23, shown in FIG. 3a. Alternatively, the sterile water remains in the dialyzer according to the embodiment of FIG. 1.

Figure 4:
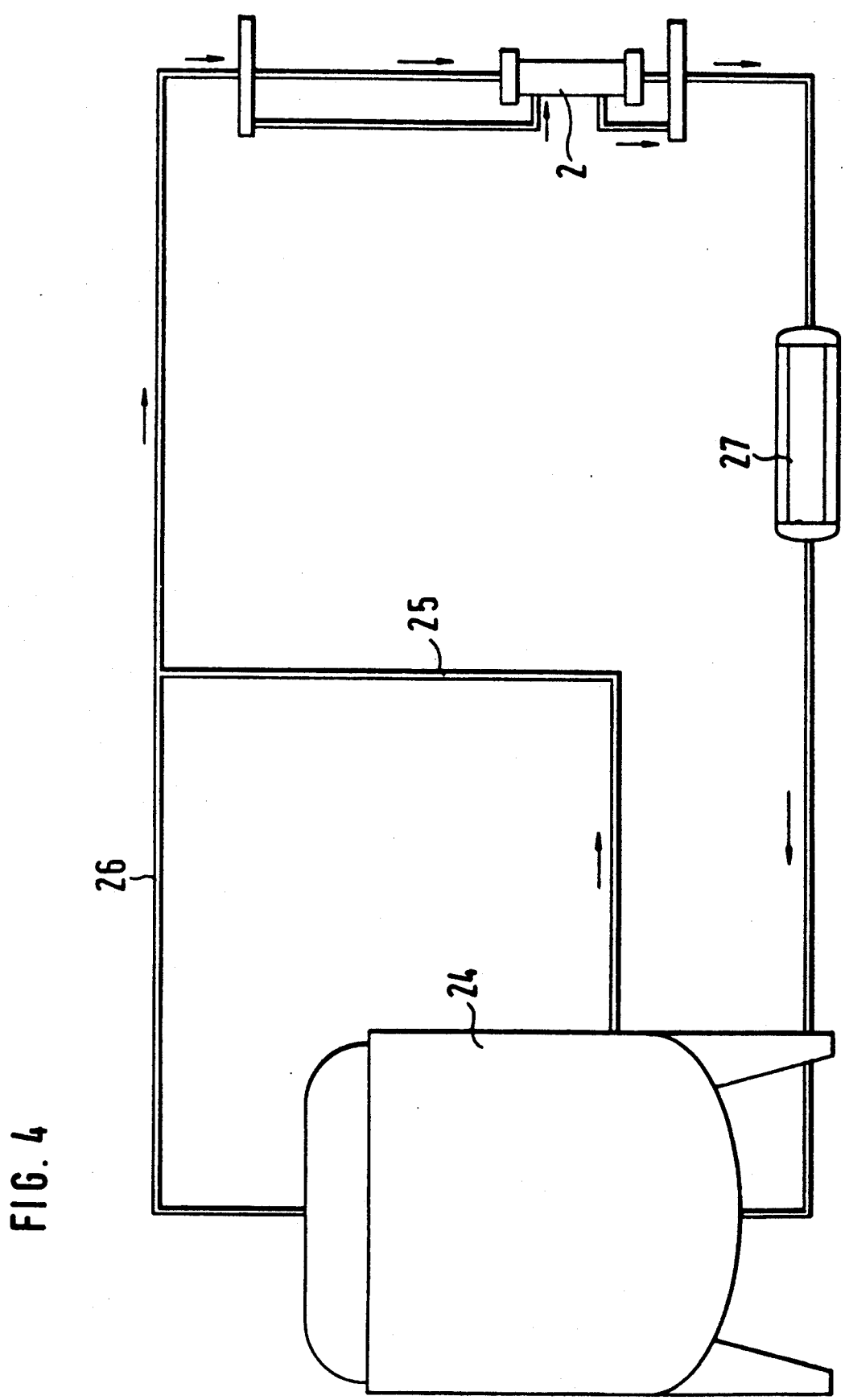
FIG. 4 shows a schematic representation of a sterilization system for dialyzers with water vapor as a sterilizing medium.

Furthermore, the sterilizing medium may be water vapor which is supplied from a vapour source 24 in accordance with the schematic representation without valves, as shown in FIG. 4. This sterilizing medium is preferably used in the case of dialyzers 2 having polysulphone membranes. As is generally known, polysulphone is hydrophobic and contains PVP (polyvinyl pyrrolidone) as the hydrophilizing agent.

By analogy with the embodiment shown in FIG. 1, dialyzer 2 is first flushed with water supplied from a corresponding source, e.g. the condensate of vapor source 24, via conduit 25. Heat sterilization is subsequently carried out with water vapor via conduit 26. The water vapor is subsequently supplied to a condenser 27. After sterilization dialyzer 2 is postflushed with sterile water, e.g. from the condensate of vapour source 24, to remove the dissolved PVP. Dialyzer 2 is subsequently dried with sterile air which is supplied by a suitable source and fed into the system, e.g. according to FIG. 3a.

The technical implementation of the above-mentioned steps and the provision of the necessary control can be carried out by those skilled in the art on the basis of the given steps and in accordance with the described embodiment according to FIG. 1 without any inventive efforts being required. For instance, the cooling phase is dispensed with when peracetic acid is used as the sterilizing medium for treatment at room temperature according to FIG. 3. In such a case, a corresponding cooler 12 either does not exist or is not switched on in the system.

We claim:

1. A method for sterilizing a medical unit comprising at least two connections for a fluid flow pathway where a sterilizing medium flows through said unit, comprising the steps of:
   (a) inserting a medical unit comprising at least two connections into a sterilization system under pressure-tight coupling of said at least two connections to a feed conduit and a discharge conduit under atmospheric conditions;
   (b) passing a sterilizing medium from said sterilization system through said medical unit for a given period of time;
   (c) closing said at least two connections in the coupled state and in a germproof manner within the same being opened on completion of the sterilization operation of step (b); and
   (d) removing said medical unit from said sterilization system as a sterile medical unit with said at least two connections remaining closed.

2. The method of claim 1 wherein said sterilizing medium is water vapor at a temperature of 105° C or greater.

3. The method of claim 1 wherein said sterilizing medium is a peracetic acid solution.

4. The method of claim 1 wherein prior to the treatment of said medical unit with said sterilizing medium, a fluid from said sterilization system is flushed through said medical unit.

5. The method as of claim 4 wherein said fluid is water.

6. The method of claim 1 wherein on completion of the sterilization operation said medical unit is flushed with a sterile fluid prior to the closing of said at least two connections.

7. The method of claim 6 wherein said sterile fluid is water.

8. The method of claim 7 wherein said sterile fluid is a cooled sterilizing medium.

9. The method of claim 6 wherein said sterile fluid is a cooled sterilizing medium.

10. The method of claim 6 wherein at least a part of said sterile fluid remains in said medical unit when said at least two connections are closed.

11. The method of claim 1 wherein a drying operation with a sterile gas is carried out prior to closing said at least two connections of said medical unit.

12. The method of claim 11 wherein said sterile gas is air at a temperature of 100° C. or greater.

13. A method of sterilizing a medical unit having at least two connections for a fluid flow pathway wherein a sterilizing medium flows through said medical unit, said method comprising the steps of:

(a) inserting and temporarily fastening a medical unit having at least two connections in a closed sterilization system defining a circuit under pressure-tight coupling of one of said at least two connections to a feed conduit and the other of said at least two connections to a discharge conduit under atmospheric conditions;

(b) passing a sterilizing medium to said feed conduit, through said medical unit, and into said discharge conduit for a given period of time;

(c) closing said at least two connections upon completion of the sterilization operation of step (b) in the coupled state and in a germproof manner without said at least two connections being opened to the atmosphere; and (d) removing said medical unit from said sterilization system as a sterile medical unit with said at least two connections remaining closed.

14. The method of claim 13 wherein said sterilizing medium is pressurized water at a temperature of about 105° C. or greater.

15. The method of claim 13 wherein said sterilizing medium is a peracetic acid solution.

16. The method of claim 13 wherein prior to the treatment of said medical unit with said sterilizing medium, a fluid from said sterilization system is flushed through said medical unit.

17. The method of claim 16 wherein said fluid is water.

18. The method of claim 13 wherein upon completion of the sterilization operation, said connected medical unit is flushed with a sterile fluid until said at least two connections are closed.

19. The method of claim 18 wherein said sterile fluid is water.

20. The method of claim 18 wherein said sterile fluid is a cooled sterilizing medium.

21. The method of claim 18 wherein at least a part of said sterile fluid remains in said medical unit when said at least two connections are closed.

22. The method of claim 13 wherein a drying operation with a sterile gas is carried out prior to closing said at least two connections of said medical unit.

23. The method of claim 22 wherein said sterile gas is air at a temperature of 100° C. or greater.

* * * * *